United States Patent
Mouawad

(10) Patent No.: US 11,002,001 B2
(45) Date of Patent: May 11, 2021

(54) METHOD OF ENGINEERING MONOLITHIC EARTHEN MASONRY

(71) Applicant: Dani Mouawad, Cary, NC (US)

(72) Inventor: Dani Mouawad, Cary, NC (US)

( * ) Notice: Subject to any disclaimer, the term of this patent is extended or adjusted under 35 U.S.C. 154(b) by 141 days.

(21) Appl. No.: 16/565,831

(22) Filed: Sep. 10, 2019

(65) Prior Publication Data

US 2021/0071408 A1    Mar. 11, 2021

(51) Int. Cl.
| | | |
|---|---|---|
| *E04B 1/00* | (2006.01) | |
| *E04C 3/36* | (2006.01) | |
| *E04C 1/40* | (2006.01) | |
| *G01N 33/24* | (2006.01) | |

(52) U.S. Cl.
CPC ............. *E04B 1/0007* (2013.01); *E04C 1/40* (2013.01); *E04C 3/36* (2013.01); *G01N 33/24* (2013.01)

(58) Field of Classification Search
CPC ............ E04B 1/0007; E04C 1/40; E04C 3/36; G01N 33/24
See application file for complete search history.

(56) References Cited

U.S. PATENT DOCUMENTS

| | | | | |
|---|---|---|---|---|
| 4,947,611 | A * | 8/1990 | Otsuka | E04C 2/16 52/745.05 |
| 5,161,341 | A * | 11/1992 | Gilles | B28C 5/1238 52/309.17 |
| 5,668,306 | A * | 9/1997 | Doherty | G01N 15/08 73/38 |
| 9,803,382 | B1 * | 10/2017 | Mouawad | E04G 17/0652 |
| 2014/0352251 | A1 * | 12/2014 | Jung | E04G 11/085 52/742.13 |

\* cited by examiner

*Primary Examiner* — Ryan D Walsh

(57) ABSTRACT

A method of engineering monolithic earthen masonry consists of selecting sufficient amount of subsoil mixture and straws, wherein physical characteristics of the subsoil mixture are determined from a sieve analysis test and a hydrometer analysis. The proper mixing ratios of the subsoil mixture and the straws provide a composite sample. The composite sample is then dried and lastly exposed to a compressive test. If optimal plurality of particle size percentage distributions within the subsoil mixture is not obtainable due to lack of resources, the end-product of the non-ideal subsoil mixture is adjusted within the aforementioned method or thickness and/or height of a building to compensate for the load-bearing capacities of the building.

13 Claims, 9 Drawing Sheets

US 11,002,001 B2

METHOD OF ENGINEERING MONOLITHIC EARTHEN MASONRY

FIELD OF THE INVENTION

The present invention relates generally to a method for creating earthen-composite mixture and structures from the mixture. More specifically, the present invention is a method for creating a monolithic engineered earthen masonry mixture from composite earthen materials for testing the mixture and for building structures with the mixture as the method is both understood by structural engineers and by building code regulators.

BACKGROUND OF THE INVENTION

In present society, it is understood that construction work is a basic factor of almost all successful societies. Construction work can include the construction of homes, buildings, and other similar structures. Construction work can include a wide variety of building materials from brick and mortar to earthen composites. Construction work utilizing modern building materials like brick and mortar or concrete is regulated and standardized with methods that are equally understood by structural engineers and building code regulators or inspectors. Also, these methods are capable of repeatedly producing the same results. However, for construction work that need to utilize earthen materials, there are no standards or methods on a similar level of sophistication as to those standards and methods previously mentioned for modern construction work. Currently, there is no method of construction for structural engineers to utilize earthen composite materials to repeatedly produce the same results. Also, there is no method of construction for structures made of earthen composite materials in which building code regulators or inspectors can understand and follow.

An objective of the present invention is to provide both structural engineers and building code regulators or inspectors with a repeated and easily comprehensible method for creating a masonry mixture from earthen composite materials. The present invention intends to provide users with a method in which the masonry mixtures can be consistent and replicable with the near same result. The present invention intends to provide users with a method in which the masonry mixture can be obtained from local source material. Another objective of the present invention is to provide both structural engineers and building code regulators or inspectors with an easily comprehensible method of testing the masonry mixture to ensure that the mixture is supported by current building codes, regulations, or other similar standards. Another objective of the present invention is to provide users with an easily comprehensible method for utilizing the masonry mixture in construction of structures.

SUMMARY OF THE INVENTION

The present invention is a series of methods for creating, testing, and utilizing a masonry mixture from earthen composite materials. The present invention intends to provide users with a method for creating a masonry mixture with the same result each time. The present invention presents the method of creating the masonry mixture in a manner that is understood by both the user creating the mixture and by the user who must inspect the mixture. The present invention provides a method for testing and adjusting the masonry mixture that is understood by both the user creating the mixture and by the user who must inspect the mixture. The present invention provides a method for constructing structures with the masonry mixture that is understood by both the user creating the structures and by the user who must inspect the structures.

DETAIL DESCRIPTIONS OF THE INVENTION

All illustrations of the drawings are for the purpose of describing selected versions of the present invention and are not intended to limit the scope of the present invention.

Monolithic Engineered Earthen Masonry (MEEM) is a scientific methodology applicable to vast variety of local subsoils as building material sources. Technical approach for MEEM relies on known scientific procedures and structural engineering methodologies that conform with the International Building Code. Ecological approach for MEEM allows the usage of the most abundant resource (earth) to provide safe, reliable, replicable, and durable engineering designs. The purpose of the present invention is to provide supportive scientific tools for structural engineers and a reliable procedure manual that code reinforcing officials can use as a guideline. The basic Ingredients of MEEM are the same as "cob" (Subsoil, Sand, Straw and water). This anecdotal ancient method of building that withstood for millennium the challenge of time, needed a scientific approach to support our current Structural Engineering Community and a reliable yet practical procedure manual for Code Reinforcing Officials.

Figure 1:
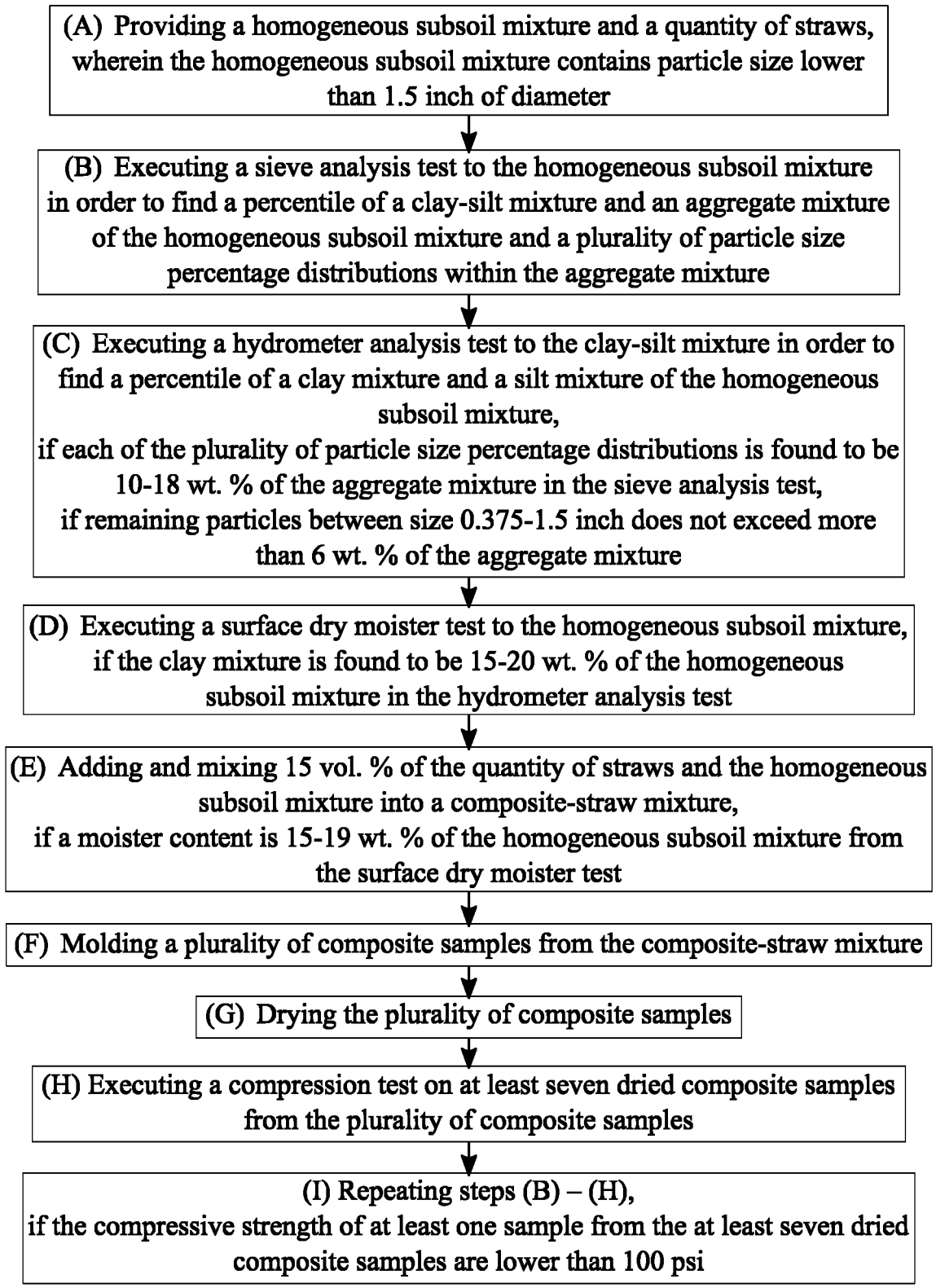
FIG. 1 is an illustration showing the overall method of the present invention from the homogeneous subsoil mixture to the compression test passing sample.

The present invention is a method of engineering monolithic earthen masonry so that the outlined method can be adapted as a procedure manual for Code Reinforcing Officials. In order to implement the present invention, a homogeneous subsoil mixture that contains particle size lower than 1.5 inch of diameter and a quantity of straws need to be provided as shown in FIG. 1 (Step A). In reference to the selection of the homogeneous subsoil mixture, all topsoil and organic materials is removed from a subsoil to be used within the present invention, regardless of the sources of the subsoil. The subsoil can be obtained from the site of construction such as excess from grading, modified landscaping, excavation of new pond, and the like or from offsite such as nearby construction or compiled subsoil. Preferably, the subsoil comes from one source and be visually as homogenous as possible. In the event the selected subsoil originates from more than one source or the geological nature of the same subsoil appears to be visually heterogeneous, the entire subsoil collection is mixed, via tractor or any other mixing apparatus, until the entire subsoil collection becomes homogenous in appearance. Once the homogeneous appearance of the subsoil in confirmed, the subsoil is considered as the homogeneous subsoil mixture of the present invention. However, if the heterogeneous appearance is detected within the subsoil, the corresponding subsoil is mixed thoroughly with a tractor/excavator or any other mixing apparatus. Then, the mixing process is repeated no less than 3 time until the corresponding subsoil visually appears homogeneous which in turns considers as the homogeneous subsoil mixture of the present invention. Furthermore, the homogeneous subsoil mixture is protected from rain fall, wind, and falling organic matter by covering the homogeneous subsoil mixture with a tarp, plastic materials or the like. In reference to the selection of straws, the quantity of straws can be selected from wheat or rice straw or any equivalent straw rich in silica for the region. However, hay is not recommended. The quantity of straws is visually inspected to assure that it is free from obvious decay as any decaying straws are eliminated.

A set of equally sized subsoil samples is randomly selected from the homogeneous subsoil mixture to execute the present invention for more accurate representation. Preferably 10 subsoil samples are randomly selected from the homogeneous subsoil mixture and process through the present invention to get accurate and uniform results.

Figure 2:
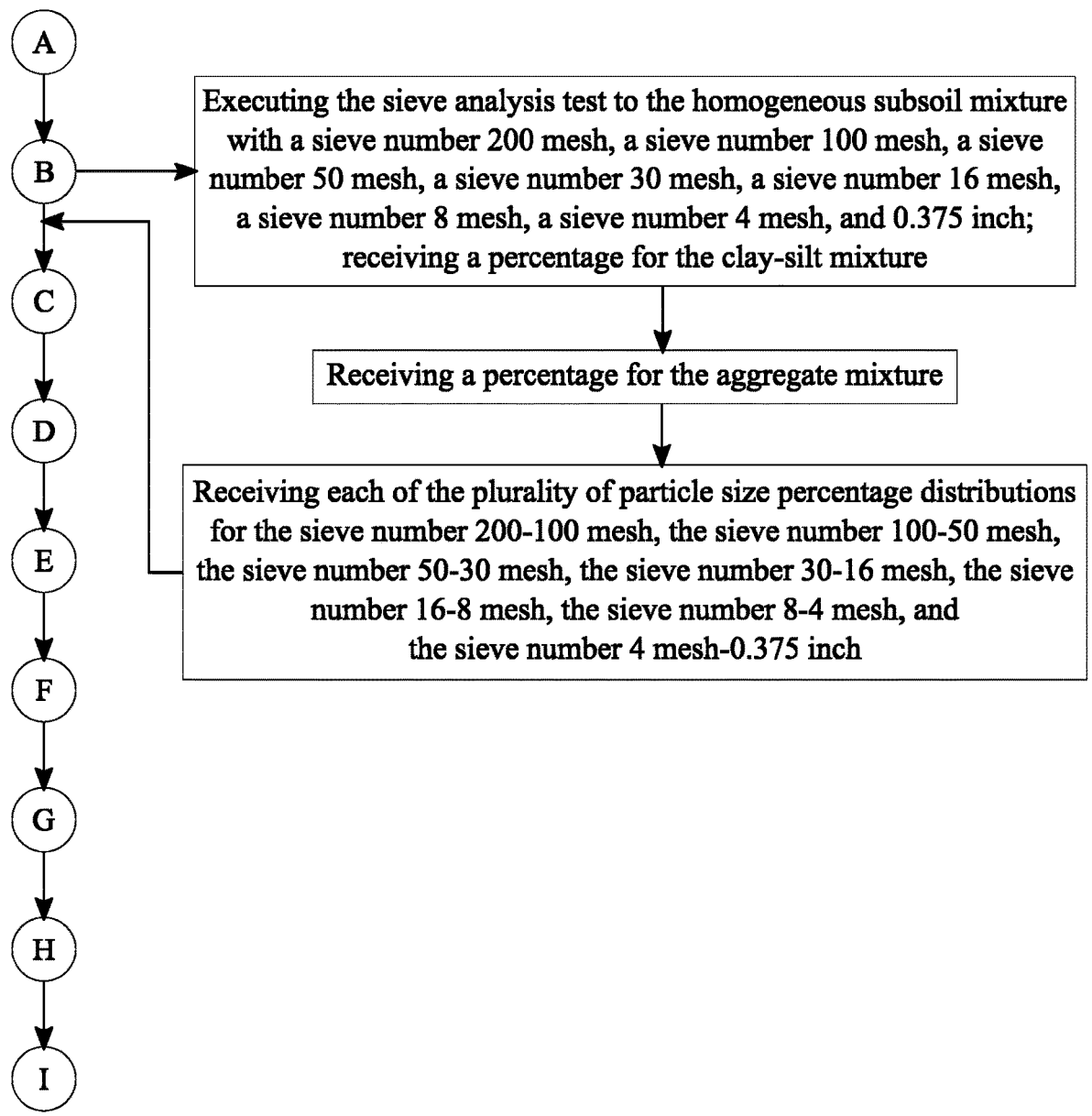
FIG. 2 is a basic flow chart illustrating further details about the sieve analysis test within the overall method.

In reference to FIG. 1-2, the present invention then executes a sieve analysis test to the homogeneous subsoil mixture extracted from the set of equally sized subsoil samples in order to find a percentile of a clay-silt mixture and an aggregate mixture of the homogeneous subsoil mixture and a plurality of particle size percentage distributions within the aggregate mixture (Step B). The homogeneous subsoil mixture undergoes the sieve analysis test as per ASTM C117, ASTM C136-AASHTO T-11, T27, or their corresponding equivalents. To assure the highest compressive strength, each of the plurality of particle size percentage distributions has to be within 10-18 wt. % of the aggregate mixture, and remaining particles between size 0.375-1.5 inch cannot exceed more than 6 wt. % of the aggregate mixture from the sieve analysis test. The plurality of particle size percentage distributions of the aggregate mixture is preferably within 14% for each sieve interval, wherein the intent is to get as close as possible to 14% for each sieve interval.

Furthermore, the sieve analysis test is executed for the homogeneous subsoil mixture with a sieve number 200 mesh, a sieve number 100 mesh, a sieve number 50 mesh, a sieve number 30 mesh, a sieve number 16 mesh, a sieve number 8 mesh, and a sieve number 4 mesh, and 0.375 inch so that the plurality of particle size percentage distributions can be obtained. Resultantly, the present invention receives each of the plurality of particle size percentage distributions for the sieve number 200-100 mesh, the sieve number 100-50 mesh, the sieve number 50-30 mesh, the sieve number 30-16 mesh, the sieve number 16-8 mesh, the sieve number 8-4 mesh, and the sieve number 4 mesh-0.375 inch. Additionally, the present invention receives a percentage for the clay-silt mixture and a percentage for the aggregate mixture from the sieve analysis test.

Figure 3:
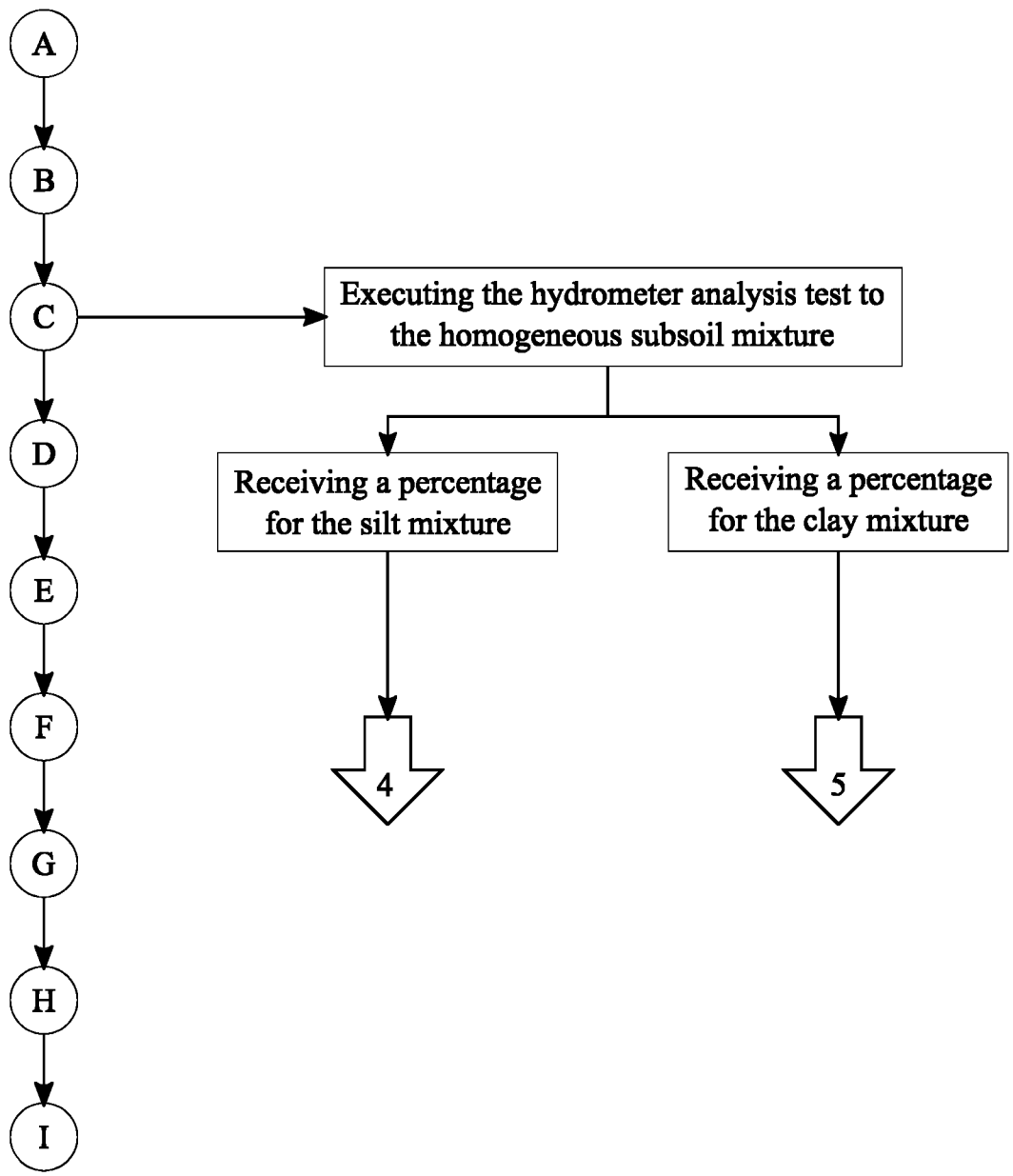
FIG. 3 is a basic flow chart illustrating further details about the hydrometer analysis test within the overall method.

In reference to FIG. 1 and FIG. 3, the present invention then executes a hydrometer analysis test to the clay-silt mixture in order to find a percentile of a clay mixture and a silt mixture of the homogeneous subsoil mixture (Step C). The hydrometer analysis, preferably ASTM D421/422 or their corresponding equivalents is utilized within the present invention for two main reasons. First, the hydrometer analysis test determines the percentile of the clay and silt that is finer than the sieve number 200 mesh. Secondly, the hydrometer analysis test help to determine slight increments of the amount of clay when the silt content is elevated, considering that elevated silt content has a negative impact (even if minimal) on the clay stabilizing capacity. More specifically, when the hydrometer analysis test is executed to the homogeneous subsoil mixture, a percentage for the clay mixture and a percentage for the silt mixture are received within the present invention so that the next step of the present invention can be determined.

In reference to FIG. 1, the present invention then executes a surface dry moister test to the homogeneous subsoil mixture if the percentile of the clay mixture is found to be 15-20 wt. % of the homogeneous subsoil mixture from the hydrometer analysis test (Step D). However, a first supplementary mixture and a second supplementary mixture are required to be introduced within the present invention if the percentile of the clay mixture is more than 20 wt. % or less than 15 wt. % of the homogeneous subsoil mixture.

Figure 4:
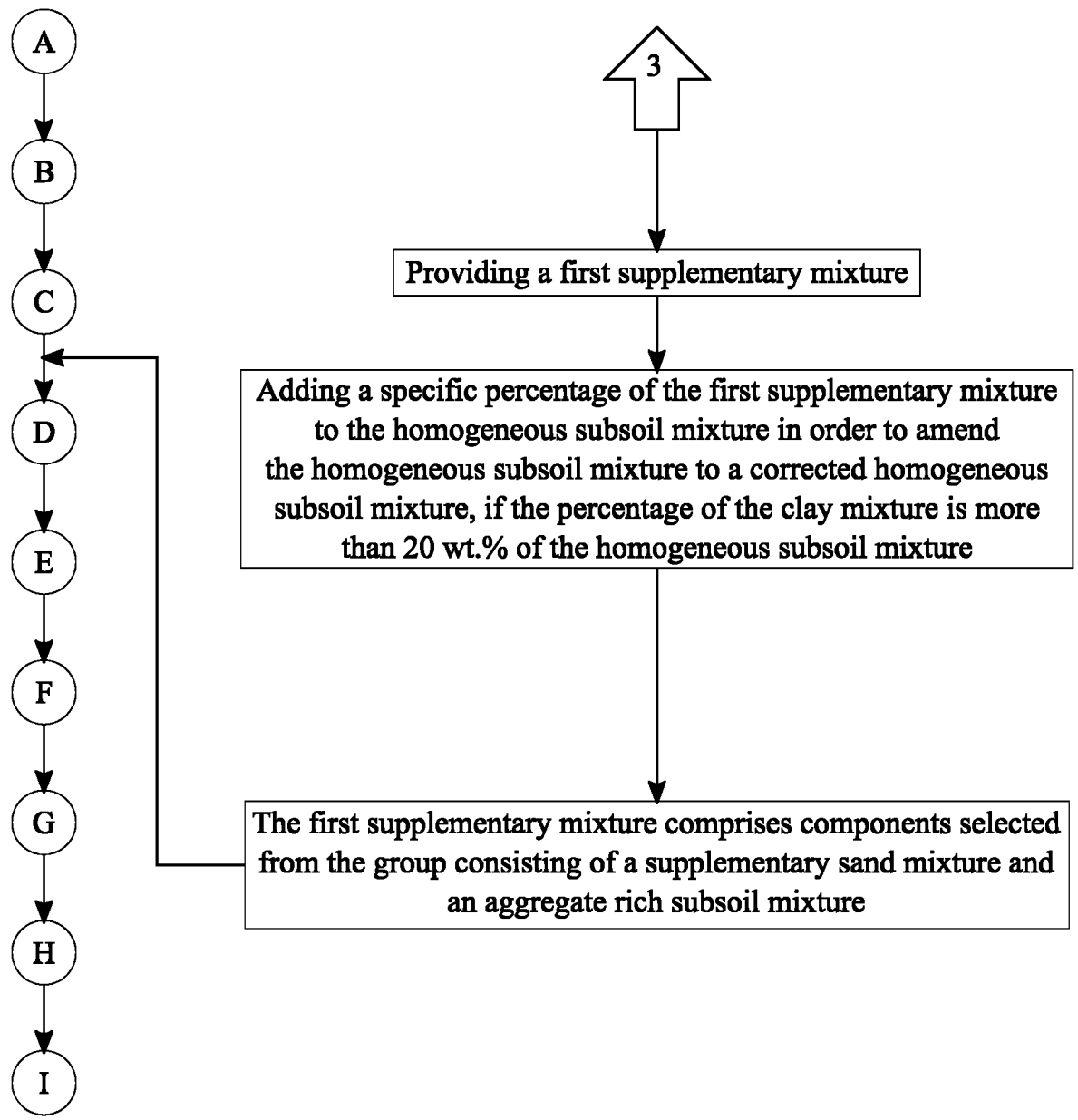
FIG. 4 is a basic flow chart illustrating further details about the first supplementary mixture within the overall method.

In reference to FIG. 4, if the percentile of the clay mixture comes out to be more than 20 wt. % of the homogeneous subsoil mixture through the hydrometer analysis test, a specific percentage of the first supplementary mixture is added to the homogeneous subsoil mixture in order to amend the homogeneous subsoil mixture to a corrected homogeneous subsoil mixture. The first supplementary mixture is provided within the present invention to overcome the excess amount of the clay mixture within the homogeneous subsoil mixture, wherein the first supplementary mixture comprises components selected from the group consisting of a supplementary sand mixture and an aggregate rich subsoil mixture.

Figure 5:
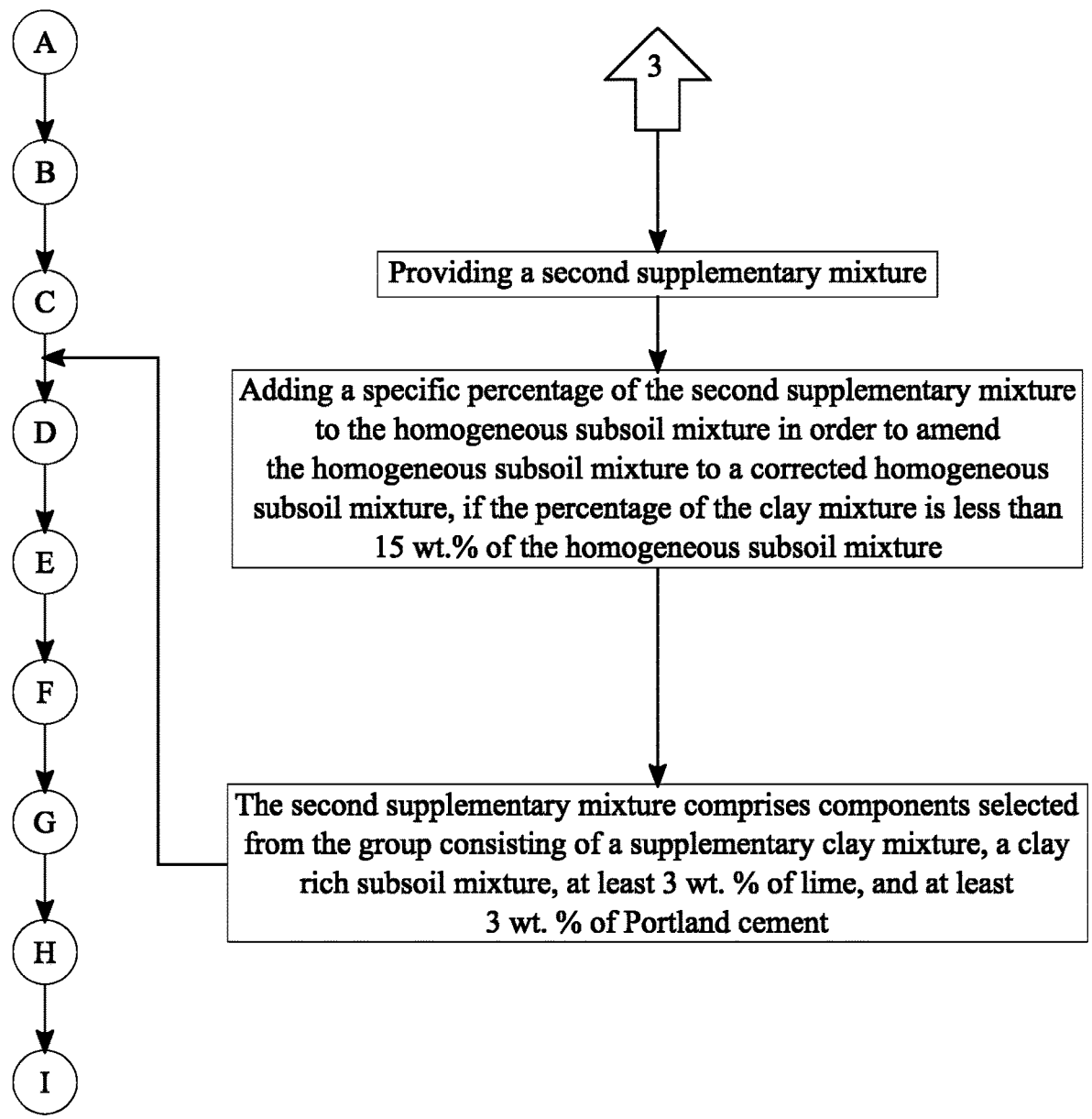
FIG. 5 is a basic flow chart illustrating further details about the second supplementary mixture within the overall method.

In reference to FIG. 5, if the percentile of the clay mixture comes out to be less than 15 wt. % of the homogeneous subsoil mixture through the hydrometer analysis test, a specific percentage of the second supplementary mixture is added to the homogeneous subsoil mixture in order to amend the homogeneous subsoil mixture to a corrected homogeneous subsoil mixture. The second supplementary mixture is provided within the present invention to overcome the deficient amount of the clay mixture within the homogeneous subsoil mixture, wherein the second supplementary mixture comprises components selected from the group consisting of a supplementary clay mixture, a clay rich subsoil mixture, at least 3 wt. % of lime (processed limestone powder), and at least 3 wt. % of Portland cement. Additionally, the supplementary clay mixture and the clay rich subsoil mixture function as stabilizing agent and the at least 3 wt. % of lime and the at least 3 wt. % of Portland cement function as bonding agent.

The present invention uses the clay mixture and the aggregate mixture as stabilizing agent and load bearing agents, respectively. In reference to FIG. 1, the clay mixture and the aggregate mixture are mixed into a dry composite mixture if each of the plurality of particle size percentage distributions is found to be 10-18 wt. % of the aggregate mixture through the sieve analysis test and the percentile of the clay mixture is found to be 15-20 wt. % of the homogeneous subsoil mixture through the hydrometer analysis test. The mixing process can take place manually or mechanically with a mortar mixer, through the bucket of an excavator/backhoe in an established hole in the ground, or the like. More specifically, the clay mixture and the aggregate mixture are homogenously mixed into the dry composite mixture for a first timed session using sequential flipping, folding, and smashing motions to thoroughly blend all ingredients together. The first timed session is preferably minimum of 10 minutes; however, it is not limited to 10 minutes and can determine upon the homogeneity of the homogeneous subsoil mixture.

In reference to FIG. 1, once the surface dry moister test outputs a moister content is 15-19 wt. % of the homogeneous subsoil mixture within the present invention, 15 vol. % of the quantity of straws is added and mixed to the homogeneous subsoil mixture so that a composite-straw mixture can be attained (Step E). More specifically, the quantity of straws is used to improve the tensile strength of the homogeneous subsoil mixture. The 15 vol. % of the quantity of straws is added into the homogeneous subsoil mixture and homogenously mixed together as the homogeneous subsoil mixture and the quantity of straws compose the composite-straw mixture. Furthermore, a prevailing length of a straw from the quantity of straws is larger than 4 inches so that the added tensile strength can be maximized within the present invention. The mixing process between the quantity of straws and the homogeneous subsoil mixture can take place manually or mechanically with a mortar mixer, through the bucket of an excavator/backhoe in an established hole in the ground, or the like. Preferably, the present invention utilizes a single location or apparatus to execute the mixing process between the quantity of straws and the homogeneous subsoil mixture. The mixing process between the quantity of straws and the homogeneous subsoil mixture can preferably last for minimum of 10 minutes; however, it is not limited to 10 minutes and can determine upon the homogeneity of the homogeneous subsoil mixture.

Figure 6:
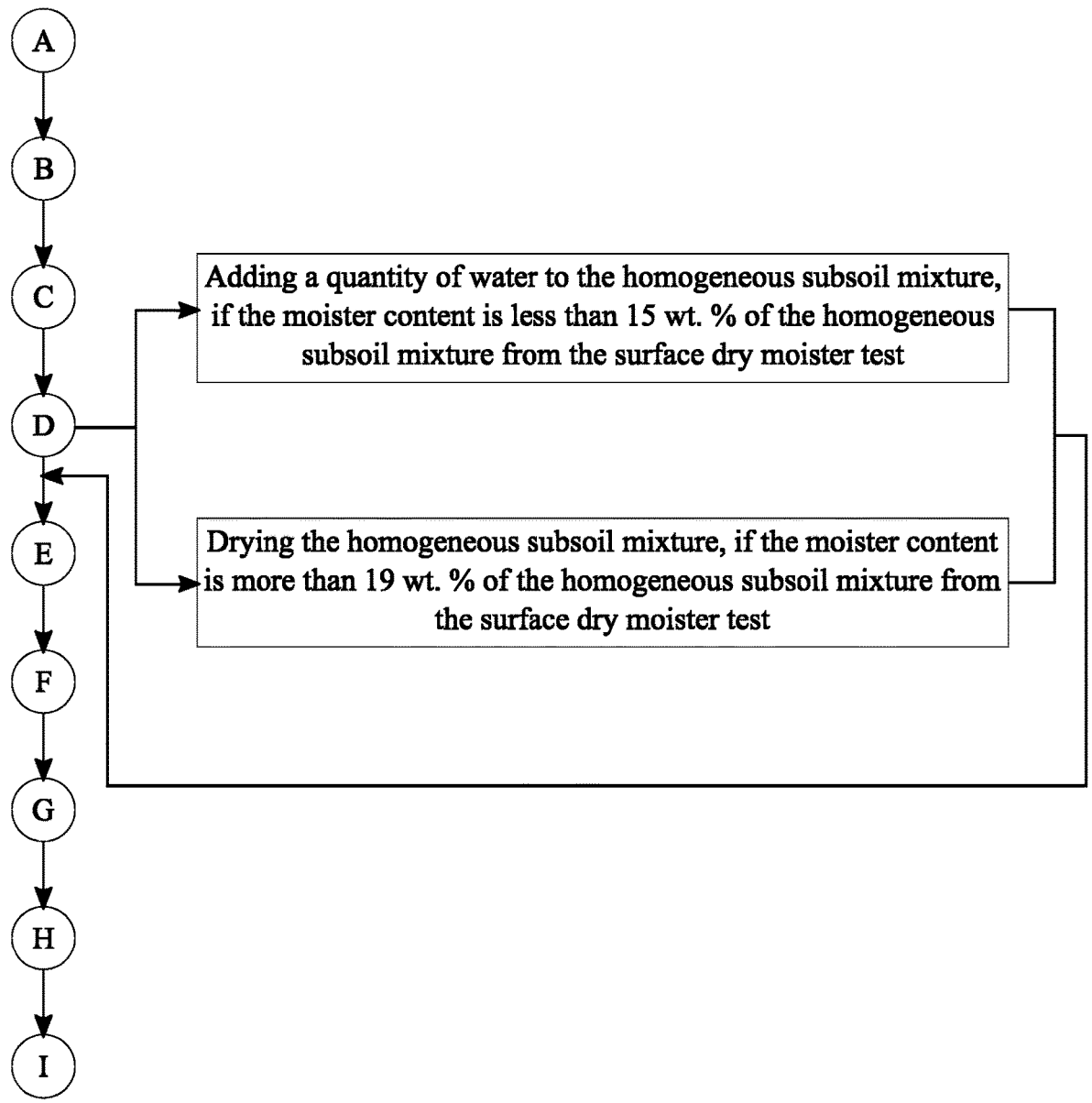
FIG. 6 is a basic flow chart illustrating further details about controlling the moister content within the overall method.
Figure 7:
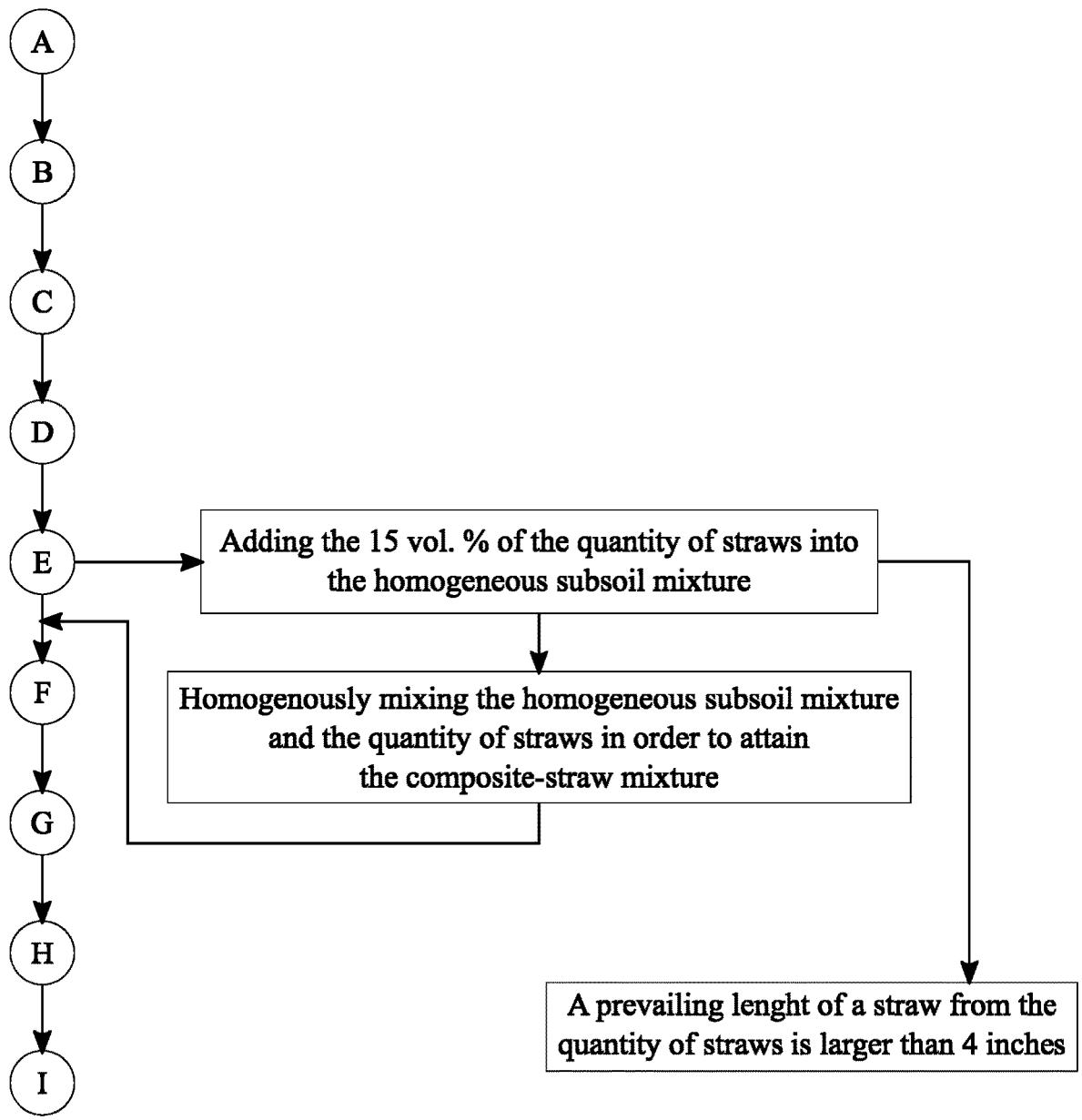
FIG. 7 is a basic flow chart illustrating further details about the quantity of straws within the overall method.

However, if the moister content is less than 15 wt. % of the homogeneous subsoil mixture, the present invention utilizes a quantity of water to dissolve and distribute the clay mixture evenly thus contributing toward homogeneous mixing process. More specifically, the quantity of water is added and homogenously mixed to the homogeneous subsoil mixture, if the moister content is less than 15 wt. % of the homogeneous subsoil mixture from the surface dry moister test as shown in FIG. 6. Furthermore, the quantity of water is required to be clean and free of debris that hinder the structural integrity of the final product of the present invention. The mixing process between the quantity of water and the homogeneous subsoil mixture can take place manually or mechanically with a mortar mixer, through the bucket of an excavator/backhoe in an established hole in the ground, or the like. Preferably, the present invention utilizes a single location or apparatus to execute the mixing process between the quantity of water and the homogeneous subsoil mixture. The mixing process between the quantity of water and the homogeneous subsoil mixture can preferably last for minimum of 10 minutes; however, it is not limited to 10 minutes and can determine upon the homogeneity of the homogeneous subsoil mixture. If the moister content is more than 19 wt. % of the homogeneous subsoil mixture, the homogeneous subsoil mixture is dried for a specific time period so that the excess moister content can be removed as shown in FIG. 6. The drying process of the homogeneous subsoil mixture can be completed with a natural process of water evaporation or mechanical apparatus that remove water particles. Once the moister content amended 15-19 wt. % of the homogeneous subsoil mixture from a lower or higher moister content, the present invention can then implement Step E before proceeding the next step of the present invention.

Figure 9:
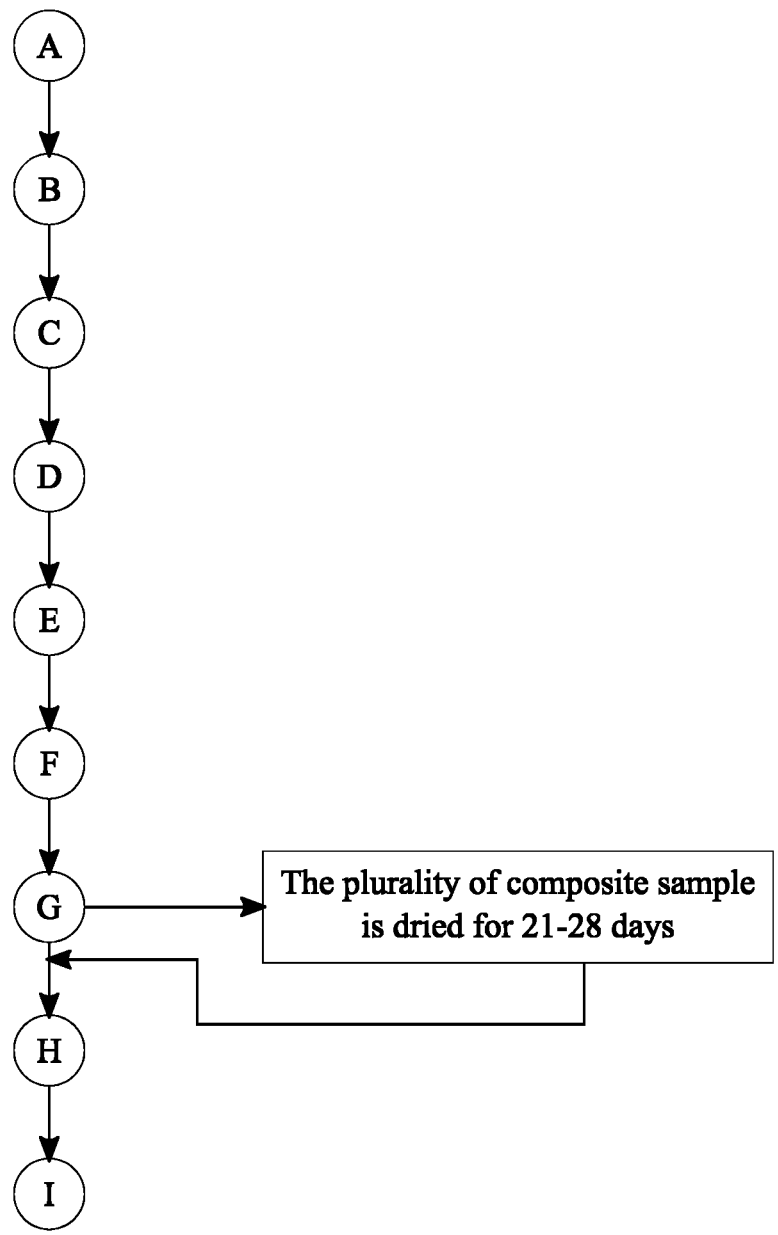
FIG. 9 is a basic flow chart illustrating further details about the composite sample drying process within the overall method.

In reference to FIG. 1 and FIG. 9, a plurality of composite samples is molded from the composite-straw mixture (Step F). After, the plurality of composite samples is molded, the plurality of composite samples is dried (Step G) before proceeding the next step of the present invention. The drying process of the plurality of composite samples is preferably 21-28 days as the total number of days depend upon many different environmental factors such as humidity and temperature. More specifically, a minimum of ten 4 inch diameter cylinders ought to be filled with the composite-straw mixture as follows; The composite-straw mixture is compacted in 6-7 stages, for each of the 10 cylinders, by following the same compaction method, weight and frequencies as per "Standard Proctor Test", to assure proper compaction and to prevent voids within the testing sample. Then, any excess material of the composite-straw mixture beyond the upper edge of the cylinder is removed and leveled by using a wetted wooden plank as the wooden plank is moved back and forth motion. All cylinders are removed from their molds after 3-5 days based on the level of local humidity. More specifically, as they demonstrate sufficient signs of shrinkage, the plastic cylinders are place one by one upside down on ¼" metal lath that permit better ventilation. Afterward the drying composite-straw mixture is fully exposed to air as the plastic cylinders are gently and vertically removed. Afterward the plurality of composite samples are rotated upside down on a weekly base till the same is exposed to the compression test.

Figure 8:
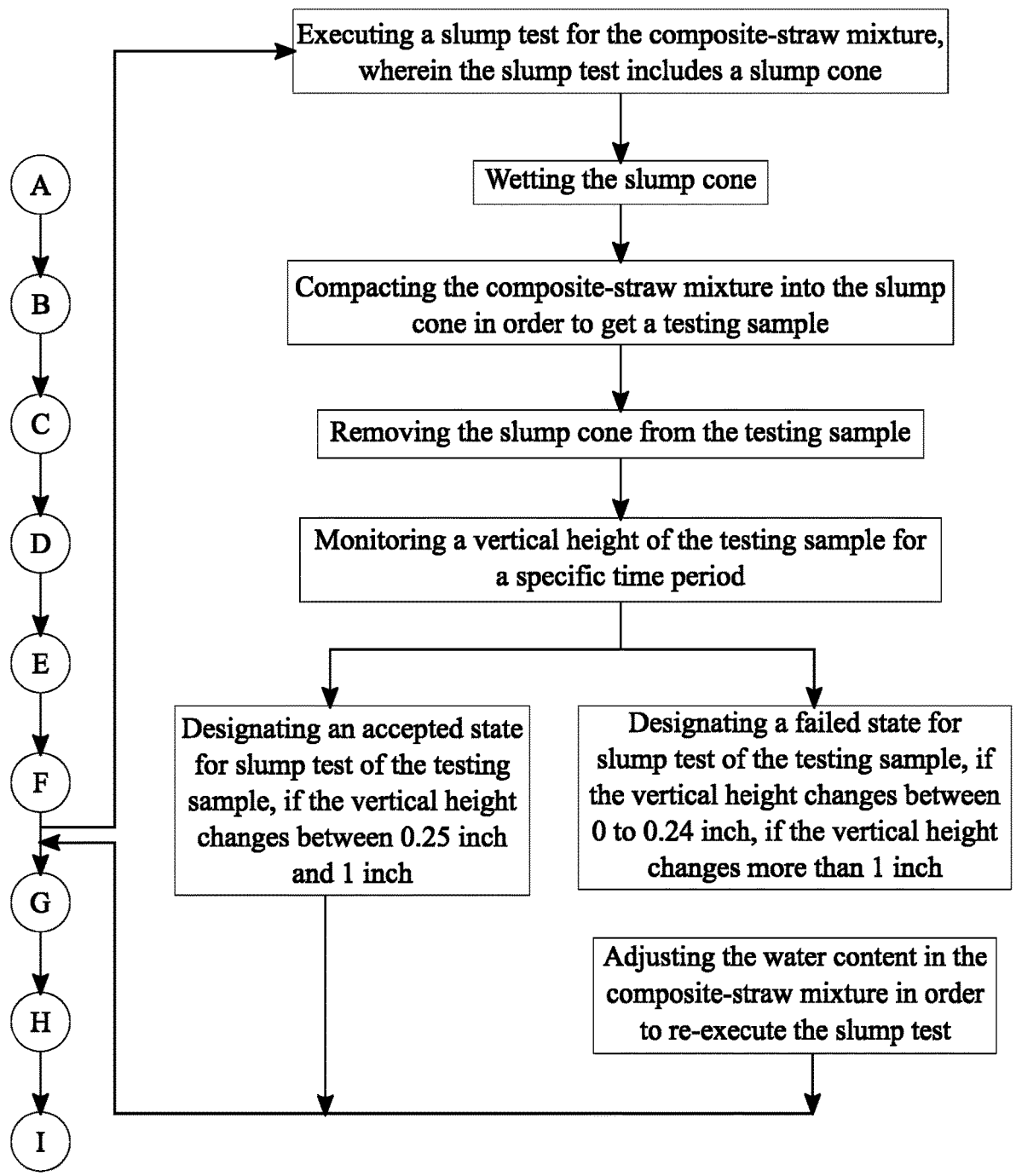
FIG. 8 is a basic flow chart illustrating further details about the slump test within the overall method.

In reference to FIG. 8, a slump test (modified ASTM C-143) is executed for the composite-straw mixture before proceeding to Step G in order to validate the proper content of water and viscosity of the composite-straw mixture. In order to execute the slump test, a slump cone is provided within the present invention. The slump test is as follows; first, the slump cone and the surface area where it contacts the composite-straw mixture is wetted to prevent stickiness and deformity of a testing sample. The slump cone is then placed in upside down position (a narrow rim facing down) in a secure and stable position to avoid tilting. The composite-straw mixture is compacted in 6-7 stages, by following the same compaction method, weight and frequencies as per "Standard Proctor Test", to assure proper compaction and to prevent voids within the testing sample. Then, any excess material of the composite-straw mixture beyond a wider rim of the slump cone is removed and leveled by using a wetted wooden plank as the wooden plank is moved back and forth motion. The slump cone is then reversed upside down, after both openings are tightly sealed, where the wider rim is facing down. At this point, the slump cone is slowly and vertically removed away from the composite-straw mixture in a sliding motion. Once the slump cone is removed, the testing sample of the composite-straw mixture is available to monitor a vertical height for a specific time period that generally indicates the pass and fail circumstances of the slump test. More specifically, the related ASTM rod is then placed on top of the slump cone and measure the vertical distance between the top of the slump cone and the top of the testing sample within the first 3 minutes of the removal of the slump cone such that the specific time period is 3 minutes.

If the vertical height changes between 0.25 inch and 1 inch, the present invention designates an accepted state for the testing sample. Then, the present invention can proceed to Step G. However, if the vertical height changes between 0 to 0.24 inch or more than 1 inch, the present invention designates a failed state for the testing sample. The water content in the composite-straw mixture is then adjusted and re-executes the slump test until the accepted state is attained for the testing sample. Then, the present invention can proceed to Step G.

When the plurality of composite samples is dried within the present invention, the plurality of composite samples is recognized as dried composite samples. In reference to FIG. 1, the present invention then executes a compression test on the at least seven dried composite samples from the plurality of composite samples so that the at least seven dried composite samples can be deemed pass or fail (Step H). It is recommended to remove any defective or damage samples from the compression testing to get accurate results, wherein the compression test can be ASTM C39 modified, C617 modified, or their equivalent. The compression test is considered approved if the at least seven dried composite samples perform up to the recommended PSI as detailed here below.

More specifically, if the compressive strength of the at least seven dried composite samples are equal or greater than 100 psi, the at least seven dried composite samples are considered to be "construction ready". In other words, the at least seven dried composite samples reach the recommended psi of the present invention. However, if the compressive strength of at least one sample from the at least seven dried composite samples are lower than 100 psi, the at least seven dried composite samples are considered to be "not construction ready". In other words, the at least seven dried composite samples have not reached recommended psi of the present invention. In reference to FIG. 1, the present invention then repeats Steps B-H if the compressive strength of at least seven dried composite samples are lower than 100 psi (Step I). Resultantly, the present invention may be able to overcome any suboptimal distributions of the aggregate mixture in Step B, any percentile changes of the clay mixture in Step C, any moister content changes in Step D, or any quantity changes of straws in Step E. In the event, present invention is unable to reach the recommended psi, construction of a building can be slightly altered to overcome the lack of compressive strength. For example, the thickness or the height of a building can be altered to accommodate the load bearing capacities.

Monitoring and quality control: each project shall assure the proper implementation of MEEM procedure manual. The minimum requirements of the logging and recording are the following:

Name of the project
Name of the designated engineer
Name of the supervisor
Name of the certified engineering laboratory or its equivalent
Subsoil source, integrity (no topsoil, no organic materials) and homogeneity of the subsoil and the sand
Dates of all presented and issued testing procedures, if pass or fail, and corrective actions when apply,
Dates of reporting results to and from designated structural engineer
Repeating the entire testing process every 3000 cubic feet of composite
Day to day logging of proper execution of the procedure manual to include approval for; the proper implementation and sequencing of the procedure, consistency in ingredient selections, duration and quality of mixing, approval of dryness, and acceptable cavitation of the composite before proceeding to compression testing.

Making all this information available to the designated structural engineer at any time upon request and maintain records of any recommendation provided by the structural engineer as a result The content of this documentation shall become part of the record of the related building.

Although the invention has been explained in relation to its preferred embodiment, it is to be understood that many other possible modifications and variations can be made without departing from the spirit and scope of the invention as hereinafter claimed.

What is claimed is:

1. A method of engineering monolithic earthen masonry comprises the steps of:
   (A) providing a homogeneous subsoil mixture and a quantity of straws, wherein the homogeneous subsoil mixture contains particle size lower than 1.5 inch of diameter;
   (B) executing a sieve analysis test to the homogeneous subsoil mixture in order to find a percentile of a clay-silt mixture and an aggregate mixture of the homogeneous subsoil mixture and a plurality of particle size percentage distributions within the aggregate mixture;
   (C) executing a hydrometer analysis test to the clay-silt mixture in order to find a percentile of a clay mixture and a silt mixture of the homogeneous subsoil mixture,
      if each of the plurality of particle size percentage distributions is found to be 10-18 wt. % of the aggregate mixture in the sieve analysis test, and
      if remaining particles between size 0.375-1.5 inch does not exceed more than 6 wt. % of the aggregate mixture;
   (D) executing a surface dry moister test to the homogeneous subsoil mixture,
      if the clay mixture is found to be 15-20 wt. % of the homogeneous subsoil mixture in the hydrometer analysis test;
   (E) adding and mixing 15 vol. % of the quantity of straws and the homogeneous subsoil mixture into a composite-straw mixture,
      if a moister content is 15-19 wt. % of the homogeneous subsoil mixture from the surface dry moister test;
   (F) molding a plurality of composite samples from the composite-straw mixture;
   (G) drying the plurality of composite samples;
   (H) executing a compression test on at least seven dried composite samples from the plurality of composite samples; and
   (I) repeating steps (B)-(H),
      if the compressive strength of at least one sample from the at least seven dried composite samples are lower than 100 psi.

2. The method of engineering monolithic earthen masonry as claimed in claim 1 comprises the steps of:
   executing the sieve analysis test to the homogeneous subsoil mixture with a sieve number 200 mesh, a sieve number 100 mesh, a sieve number 50 mesh, a sieve number 30 mesh, a sieve number 16 mesh, a sieve number 8 mesh, a sieve number 4 mesh, and 0.375 inch;
   receiving a percentage for the clay-silt mixture;
   receiving a percentage for the aggregate mixture; and
   receiving each of the plurality of particle size percentage distributions for the sieve number 200-100 mesh, the sieve number 100-50 mesh, the sieve number 50-30 mesh, the sieve number 30-16 mesh, the sieve number 16-8 mesh, the sieve number 8-4 mesh, and the sieve number 4 mesh-0.375 inch.

3. The method of engineering monolithic earthen masonry as claimed in claim 1 comprises the steps of:
executing the hydrometer analysis test to the homogeneous subsoil mixture;
receiving a percentage for the clay mixture; and
receiving a percentage for the silt mixture.

4. The method of engineering monolithic earthen masonry as claimed in claim 3 comprises the steps of:
providing a first supplementary mixture;
providing a second supplementary mixture;
adding a specific percentage of the first supplementary mixture to the homogeneous subsoil mixture in order to amend the homogeneous subsoil mixture to a corrected homogeneous subsoil mixture,
if the percentage of the clay mixture is more than 20 wt. % of the homogeneous subsoil mixture; and
adding a specific percentage of the second supplementary mixture to the homogeneous subsoil mixture in order to amend the homogeneous subsoil mixture to a corrected homogeneous subsoil mixture,
if the percentage of the clay mixture is less than 15 wt. % of the homogeneous subsoil mixture.

5. The method of engineering monolithic earthen masonry as claimed in claim 4 comprises the step of:
wherein the first supplementary mixture comprises components selected from the group consisting of a supplementary sand mixture and an aggregate rich subsoil mixture.

6. The method of engineering monolithic earthen masonry as claimed in claim 4 comprises the step of:
wherein the second supplementary mixture comprises components selected from the group consisting of a supplementary clay mixture, a clay rich subsoil mixture, at least 3 wt. % of lime, and at least 3 wt. % of Portland cement.

7. The method of engineering monolithic earthen masonry as claimed in claim 1 comprises the steps of:
adding a quantity of water to the homogeneous subsoil mixture,
if the moister content is less than 15 wt. % of the homogeneous subsoil mixture from the surface dry moister test; and
drying the homogeneous subsoil mixture,
if the moister content is more than 19 wt. % of the homogeneous subsoil mixture from the surface dry moister test.

8. The method of engineering monolithic earthen masonry as claimed in claim 1 comprises the steps of:
adding the 15 vol. % of the quantity of straws into the homogeneous subsoil mixture; and
homogenously mixing the homogeneous subsoil mixture and the quantity of straws in order to attain the composite-straw mixture.

9. The method of engineering monolithic earthen masonry as claimed in claim 8 comprises the step of:
wherein a prevailing length of a straw from the quantity of straws is larger than 4 inches.

10. The method of engineering monolithic earthen masonry as claimed in claim 1 comprises the steps of:
executing a slump test for the composite-straw mixture before step (G), wherein the slump test includes a slump cone;
wetting the slump cone;
compacting the composite-straw mixture into the slump cone in order to get a testing sample;
removing the slump cone from the testing sample; and
monitoring a vertical height of the testing sample for a specific time period.

11. The method of engineering monolithic earthen masonry as claimed in claim 10 comprises the step of:
designating an accepted state for slump test of the testing sample, if the vertical height changes between 0.25 inch and 1 inch.

12. The method of engineering monolithic earthen masonry as claimed in claim 10 comprises the steps of:
designating a failed state for slump test of the testing sample,
if the vertical height changes between 0 to 0.24 inch,
if the vertical height changes more than 1 inch; and
adjusting the water content in the composite-straw mixture in order to re-execute the slump test.

13. The method of engineering monolithic earthen masonry as claimed in claim 1 comprises the step of:
wherein the plurality of composite samples is dried for 21-28 days.

* * * * *